(12) United States Patent
Cantley et al.

(10) Patent No.: US 6,923,795 B1
(45) Date of Patent: Aug. 2, 2005

(54) SYSTEM AND METHOD FOR ABSORBING EXCESS MENSTRUAL FLOW

(76) Inventors: April Lu Cantley, 2701 Rose Marie Dr., Bakersfield, CA (US) 93304; Harold Beal Cantley, 2701 Rose Marie Dr., Bakersfield, CA (US) 93304

(*) Notice: Subject to any disclaimer, the term of this patent is extended or adjusted under 35 U.S.C. 154(b) by 139 days.

(21) Appl. No.: 10/290,816

(22) Filed: Nov. 8, 2002

Related U.S. Application Data

(60) Provisional application No. 60/338,068, filed on Nov. 9, 2001.

(51) Int. Cl.$^7$ .............................................. A61F 13/15
(52) U.S. Cl. ............ 604/385.17; 604/354; 604/385.03; 604/387
(58) Field of Search .................. 604/317, 327–330, 604/354, 355, 358, 385.01, 385.17, 386, 604/387, 385.03, 574, 575

(56) References Cited

U.S. PATENT DOCUMENTS

| | | | |
|---|---|---|---|
| 2,683,457 A * | 7/1954 | Cunningham ................ 604/397 |
| 2,771,882 A * | 11/1956 | Leupold ................. 604/385.17 |
| 3,183,909 A * | 5/1965 | Roehr .................... 604/385.01 |
| D234,162 S * | 1/1975 | Andersen ................... D24/125 |
| 4,536,181 A * | 8/1985 | Cook ......................... 604/387 |
| 4,595,392 A | 6/1986 | Johnson et al. |
| 4,597,759 A * | 7/1986 | Johnson ................. 604/385.16 |
| 4,846,824 A * | 7/1989 | Lassen et al. .......... 604/385.17 |
| 4,919,681 A * | 4/1990 | Tyler et al. .................. 8/116.1 |
| 5,057,096 A | 10/1991 | Faglione |
| 5,169,394 A | 12/1992 | Jean |
| 5,290,262 A | 3/1994 | Vukos et al. |
| 5,295,984 A | 3/1994 | Contente et al. |
| 5,336,208 A | 8/1994 | Rosenbluth et al. |
| 5,484,429 A * | 1/1996 | Vukos et al. .......... 604/385.23 |
| D368,519 S * | 4/1996 | Harrison et al. ........... D24/125 |
| 5,520,675 A * | 5/1996 | Knox-Sigh ............. 604/385.17 |
| 5,540,332 A * | 7/1996 | Kopacz et al. .............. 206/494 |
| 5,683,373 A * | 11/1997 | Darby ................... 604/385.01 |
| 5,713,886 A * | 2/1998 | Sturino ....................... 604/390 |
| 5,792,129 A * | 8/1998 | Johansson et al. .......... 604/387 |

(Continued)

OTHER PUBLICATIONS

Huggies Supreme Care Baby Wipes, www.huggies.com/na/procuts/supremecare.asp; 2003.*
Trademark Electronic Search System (TESS) printout, Jun. 20, 2004.*

*Primary Examiner*—Larry I. Schwartz
*Assistant Examiner*—Michael G. Bogart
(74) *Attorney, Agent, or Firm*—Walter Unterberg

(57) ABSTRACT

This invention absorbs excess menstrual flow when an intra-vaginal tampon becomes saturated during periods of heavy flow. A system of two small-size soft absorbent cloths, placed externally in the user's crotch and held in place by the female anatomy, absorbs all the excess flow. First, the multi-layer Large Cloth Assembly, inserted between and held in place by the vaginal lips at the opening of the vagina, absorbs fluid which would otherwise run down the inside of the legs when the user stands. Second, the folded Small Cloth placed on the skin between the opening of the vagina and the anus, secured in place by the buttocks closing around it, absorbs fluid which would otherwise leak through the crack between the buttocks, particulary when the body is horizontal. Disposal of both cloths is by a toilet flush. The invention has been effective in clinical trials, is medically safe, simple and hidden from view, comfortable, low cost, and adapted to any anatomy.

1 Claim, 2 Drawing Sheets

U.S. PATENT DOCUMENTS

| | | | |
|---|---|---|---|
| 6,114,597 A * | 9/2000 | Romare | 604/378 |
| 6,131,736 A * | 10/2000 | Farris et al. | 206/440 |
| 6,183,456 B1 * | 2/2001 | Brown et al. | 604/385.01 |
| 6,350,258 B1 * | 2/2002 | Markowiecki | 604/385.201 |
| 6,432,096 B1 * | 8/2002 | McFall et al. | 604/385.17 |
| 6,475,198 B1 * | 11/2002 | Lipman et al. | 604/329 |
| 6,475,203 B1 * | 11/2002 | Rubio | 604/385.03 |
| 6,632,210 B1 * | 10/2003 | Glasgow et al. | 604/385.17 |
| 6,702,796 B2 * | 3/2004 | McFall et al. | 604/385.17 |
| 2002/0058921 A1 * | 5/2002 | Sigl | 604/385.201 |
| 2002/0169433 A1 * | 11/2002 | Osborn et al. | 604/385.17 |
| 2003/0023188 A1 * | 1/2003 | Kritzman et al. | 600/575 |

* cited by examiner

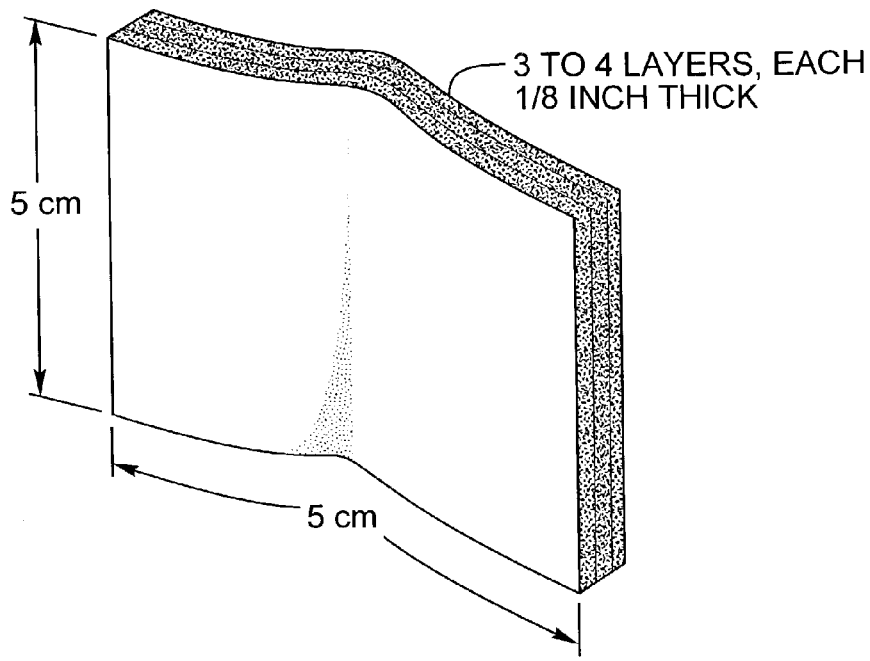
*Fig. A*
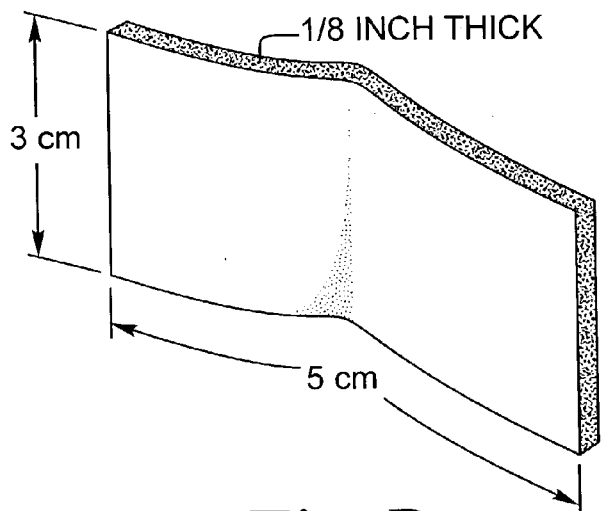
*Fig. B*
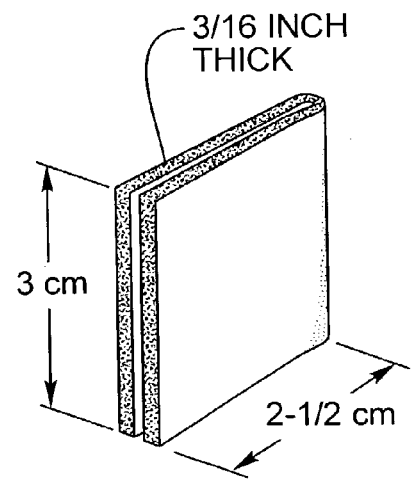
*Fig. C*

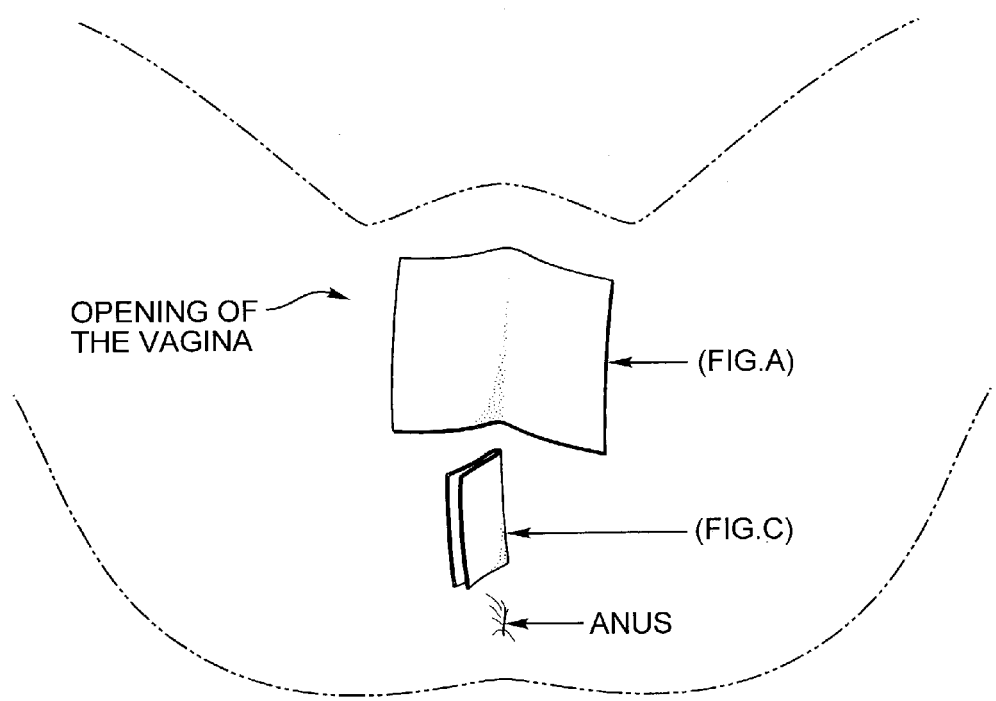
Fig. D

SYSTEM AND METHOD FOR ABSORBING EXCESS MENSTRUAL FLOW

CROSS-REFERENCE TO RELATED APPLICATIONS

This application claims the benefit of Provisional Patent Application Ser. No. 60/338,068 filed 9 Nov. 2001.

BACKGROUND OF THE INVENTION—FIELD OF THE INVENTION

This invention relates generally to absorption of women's menstrual blood flow. More particularly, it relates to the absorption of excess flow when intra-vaginal tampons become saturated during periods of heavy flow.

BACKGROUND OF THE INVENTION—DISCUSSION OF RELATED ART

Even though highly absorbent intra-vaginal tampons are available, they should be used for only a limited time. After some four hours staphylococci bacteria growing in a blood-soaked tampon may be virulent enough to infect vaginal walls. This condition, known as Toxic Shock Syndrome (TSS), can cause a life-threatening illness in the blood stream if not properly treated.

The safer low-absorbency tampons become saturated sooner and permit excess menstrual flow to leak out of the vaginal cavity and flow downward in the crack between the buttocks. Means to absorb this excess flow have included external absorptive pads, disposable underwear, and bed chucks when lying down.

External pads do not seal off the flow completely because of their tendency to shift their position. Disposable underwear is expensive and no longer produced. Bed chucks are placed between the bedsheet and the menstruating woman, but do not stay in place as the body moves around. All these devices are bulky and require careful and environmentally proper disposal. In particular, clogging of drain pipes must be avoided.

Accordingly, an improved invention for the effective control of excess menstrual flow was sought which would fulfil the following objects.

OBJECTS OF THE INVENTION

1. To be medically safe;
2. To be straightforward to use;
3. To be highly absorptive;
4. To be small and hidden from view;
5. To provide maximum comfort to the user;
6. To be easily disposable;
7. To be simple to produce and inexpensive; and
8. To be versatile and fit various body anatomies.

SUMMARY OF THE INVENTION

The instant invention was devised to implement the objects stated above. The system of the invention comprises two configurations of small-size, soft, absorbent cloths placed externally at locations in the female crotch region where excess menstrual flow can be best absorbed. Both configurations are held in place by the female anatomy without any attach devices. These two cloth configurations act in concert to absorb all the excess menstrual flow and prevent it from reaching other body parts, clothing and the environment.

The cloth material is composed of pulp and polypropylene, commercially obtainable as Huggies Supreme Care® baby wipes which are hypo-allergenic and fragrance-free. Both configurations use a cloth thickness of about ⅛ inch. After it has absorbed fluid, this cloth material is disposed of by flushing down the toilet like toilet paper.

The first configuration is the Large Cloth Assembly comprising three or four adjacent flat cloth layers about 5×5 cm in surface area. It is inserted between and held in place by the vaginal lips at the opening of the vagina. When the user stands, this assembly absorbs fluid which would otherwise run down the inside of the legs.

The second configuration is the Small Cloth, a single cloth layer with a surface area of about 3×5 cm. For use this layer is folded in two to a reduced surface area of about 3×2.5 cm and compressed to a thickness of about 3/16 inch from the uncompressed double layer of about 2×⅛ inch. This folded Small Cloth is placed snug against the skin between the opening of the vagina and the anus, secured in place by the buttocks closing around it, with each folded half facing one of the buttocks. This configuration absorbs fluid which would otherwise leak through the crack between the buttocks, particularly when the body is horizontal.

Clinical trials have confirmed the effectiveness of this two-cloth system. Specific advantages include:

1. Medically safe—hypo-allergenic, allows normal body functions and reduces the risk of Toxic Shock Syndrome (TSS). The escape of menstrual fluid is not impeded, but merely absorbed.
2. Straightforward use—cloths are small and easily manipulated, folded over a finger for insertion. The finger does not touch any fluid.
3. Highly absorptive—cloths are made of cellulose fiber much like a soft cotton sponge.
4. Small and hidden—the cloths are transportable in purse or pocket and when in place are hidden from view and do not show.
5. Maximum comfort—cloths are small and soft, remain outside body, and are held in place naturally.
6. Easily disposable—cloths are meant to be flushed down toilet like toilet paper and will not obstruct drains.
7. Simple to produce and inexpensive—cloths made of known low cost materials and can be simply packaged.
8. Versatile—different female anatomies are easily accommodated as the cloths are placed where excess fluid can be best absorbed.

BRIEF DESCRIPTION OF THE SEVERAL VIEWS OF THE DRAWING

A better understanding of the invention may be gained by reference to the Detailed Description which follows, in conjunction with Figures A though D which show the components of the invention and their application. In the drawing FIG. A shows views of the Large Cloth Assembly;

FIG. B shows views of the unfolded Small Cloth;

FIG. C shows a view of the folded Small Cloth;

FIG. D shows the female crotch region from the vagina opening to the anus with the Large Cloth Assembly in place over the opening of the vagina, and the folded Small Cloth in place against the skin between the opening of the vagina and the anus.

DETAILED DESCRIPTION OF THE INVENTION

Referring now to FIG. A, the Large Cloth Assembly is shown to comprise three or four adjacent layers of a about ⅛ inch thick soft absorbent flat cloth about 5 cm×5 cm in surface area.

Referring now to FIG. B, the unfolded Small Cloth is a layer of about ⅛ inch thick soft absorbent cloth about 3 cm×5 cm in surface area.

Referring now to FIG. C, the folded and compressed Small Cloth is shown, with a surface area of now about 3 cm×2.5 cm and compressed to a thickness of about 3/16 inch from the uncompressed double layer of about 2×⅛ inch.

All the soft cloths are composed of pulp and polypropylene, commercially obtainable as Huggies Supreme Care® baby wipes which are hypo-allergenic and fragrance-free, and obviously safe for adults, too.

Referring now to FIG. D, the female crotch region is shown from the vagina opening to the anus. According to the Method for Absorbing Excess Menstrual Flow to be described below, the Large Cloth Assembly is in place flat over the opening of the vagina, and the folded Small Cloth is in place against the skin between the opening of the vagina and the anus.

Method for Absorbing Excess Menstrual Flow

The method of the invention comprises placing small size absorbing soft cloths on specific places in the female crotch region where excess menstrual flow occurs. In the embodiment disclosed here two cloths, described above, are used:

1. The Large Cloth assembly of square shape is inserted between and held in place by the vaginal lips at the opening of the vagina. When the user stands, this assembly absorbs fluid which would otherwise run down the inside of the legs and soil floors and towels, typically after a bath or shower. After use it is simply flushed down the toilet like toilet paper.

2. The folded Small Cloth of rectangular shape is inserted snug against the skin between the opening of the vagina and the anus. It is secured in place by the buttocks closing around it, with each folded half facing one of the buttocks. This cloth absorbs fluid which would otherwise leak through the crack between the buttocks. It is useful when the body is in a horizontal position, such as in bed. This cloth does not stick to the skin and will disengage when the buttocks are spread apart to sit on a toilet, and is also disposed of by flushing.

Used together, the Large Cloth Assembly and the Small Cloth perform an efficient job of absorbing excess menstrual flow and preventing it from reaching undesirable locations on the body, clothing or the environment. Clinical trials have confirmed the usefulness of this two-cloth system.

Advantages of the Invention

The invention described above in detail meets the objects stated earlier, with the aim of completely absorbing excess menstrual flow. Specific advantages include:

1. Medically safe—hypo-allergenic, allows normal body functions and reduces the risk of Toxic Shock Syndrome (TSS). The escape of menstrual fluid is not impeded, but merely absorbed.

2. Straightforward use—cloths are small and easily manipulated, folded over a finger for insertion. The finger does not touch any fluid.

3. Highly absorptive—cloths are made of cellulose fiber much like a soft cotton sponge.

4. Small and hidden—the cloths are transportable in purse or pocket and when in place are hidden and do not show.

5. Maximum comfort—cloths are small and soft, remain outside body, are held in place naturally without any attach devices.

6. Easily disposable—cloths are meant to be flushed down the toilet like toilet paper and will not obstruct drains.

7. Simple to produce and inexpensive—cloths are made of known low cost materials and can be simply packaged.

8. Versatile—different female anatomies are easily accommodated as the cloths are placed near the sources of excess fluid, independent of user size and shape.

It is to be understood that the invention may be realized with embodiments differing from the specific devices and method disclosed herein without departing from the scope of the present invention as delineated in the following claims.

We claim:

1. A method for the absorption of excess female menstrual blood flow using a system of small-size absorbent cloths placed in the female crotch, said system comprising a multi-layer Large Cloth Assembly and a single-layer Small Cloth, said method comprising the steps of:

a. using a finger to insert the Large Cloth Assembly between vaginal lips at an opening of a vagina where said lips hold the Large Cloth Assembly in place;

b. folding the Small Cloth in two about the shorter centerline and compressing it slightly;

c. using a finger to place the compressed folded Small Cloth snug against a skin between said opening of a vagina and an anus, and securing said folded Small Cloth in place by closing buttocks around said folded Small Cloth;

d. using a finger to remove the Large Cloth Assembly when containing absorbed fluid and flushing the Large Cloth Assembly down a toilet for disposal; and e. spreading buttocks to disengage the folded Small Cloth when containing absorbed fluid over a toilet and flushing the folded Small Cloth down said toilet for disposal.

* * * * *